United States Patent
Parthasaradhi Reddy et al.

(10) Patent No.: US 10,329,281 B2
(45) Date of Patent: Jun. 25, 2019

(54) POLYMORPHS AND PROCESS FOR THE PREPARATION OF QUINAZOLINYL DERIVATIVES

(71) Applicant: HETERO LABS LTD, Hyderabad (IN)

(72) Inventors: Bandi Parthasaradhi Reddy, Hyderabad (IN); Kura Rathnakar Reddy, Hyderabad (IN); Bandi Vamsi Krishna, Hyderabad (IN); Nimmala Srinivas Rao, Hyderabad (IN)

(73) Assignee: HETERO LABS LTD (IN)

( * ) Notice: Subject to any disclaimer, the term of this patent is extended or adjusted under 35 U.S.C. 154(b) by 0 days.

(21) Appl. No.: 15/565,996

(22) PCT Filed: Apr. 15, 2016

(86) PCT No.: PCT/IB2016/052164
§ 371 (c)(1),
(2) Date: Oct. 12, 2017

(87) PCT Pub. No.: WO2016/166720
PCT Pub. Date: Oct. 20, 2016

(65) Prior Publication Data
US 2018/0194754 A1    Jul. 12, 2018

(30) Foreign Application Priority Data

Apr. 17, 2015  (IN) ............... 1979/CHE/2015
Dec. 30, 2015  (IN) ............... 7060/CHE/2015

(51) Int. Cl.
*C07D 405/12*  (2006.01)
*A61K 31/517*  (2006.01)
*C07C 57/145*  (2006.01)

(52) U.S. Cl.
CPC .......... *C07D 405/12* (2013.01); *A61K 31/517* (2013.01); *C07C 57/145* (2013.01); *C07B 2200/13* (2013.01)

(58) Field of Classification Search
CPC ................... C07D 405/12; A61K 31/517
USPC ............................ 544/293; 514/266.2
See application file for complete search history.

(56) References Cited

U.S. PATENT DOCUMENTS

| | | | |
|---|---|---|---|
| RE43,431 E | 5/2012 | Himmelsbach et al. | |
| 8,426,586 B2 | 4/2013 | Soyka et al. | |
| 9,630,952 B2 * | 4/2017 | Tuksar | C07D 405/12 |
| 10,011,591 B2 * | 7/2018 | Singh | A61K 31/517 |
| 2014/0051713 A1 | 2/2014 | Gidwani et al. | |

FOREIGN PATENT DOCUMENTS

| | | | | |
|---|---|---|---|---|
| CN | 104744445 A | 7/2015 | | |
| CN | 104803992 A | 7/2015 | | |
| CN | 104926800 A | 9/2015 | | |
| EP | 3023421 A1 * | 5/2016 | ........... | C07D 405/12 |
| WO | 2005037824 A2 | 4/2005 | | |
| WO | 2012121764 A1 | 9/2012 | | |
| WO | 2013052157 A1 | 4/2013 | | |
| WO | 2015007206 A1 | 1/2015 | | |
| WO | 2015103456 A1 | 7/2015 | | |
| WO | WO-2016001844 A1 * | 1/2016 | ........... | C07D 405/12 |
| WO | 2016027243 A1 | 2/2016 | | |
| WO | 2016051380 A1 | 4/2016 | | |

OTHER PUBLICATIONS

IN 201501820 I4, Jul. 28, 2017; Derwent 2017-557964 Abstract.*
International Search Report for PCT/IB2016/052164, dated Dec. 20, 2016.
Mino R. Caira, "Crystalline Polymorphism of Organic Compounds", Topics in Current Chemistry,vol. 198, Jan. 1, 1998, pp. 163-208, downloaded Oct. 11, 2017.
Disclosed Anonymously: Crystalline form of N-[4-[(3-Chloro-4-fluorophenyl) amino]-7-[[(3S)-tetrahydro-3-furanyl] oxy]-6-quinazolinyl]-4(dimethylamino)-2-butenamide and salts thereof, IPCOM000240150D, Jan. 7, 2015, downloaded Oct. 11, 2017.
Stieger, N., et al. Recrystallization of Active Pharmaceutical Ingredients. In: Marcello Andreeta (Eds.), Crystallization—Science and Technology, 2012. https://doi.org/10.5772/52725.

* cited by examiner

*Primary Examiner* — Venkataraman Balasubramanian
(74) *Attorney, Agent, or Firm* — Caesar Rivise, PC

(57) ABSTRACT

The present invention relates to Quinazolinyl derivatives polymorph, process and composition thereof. (I)

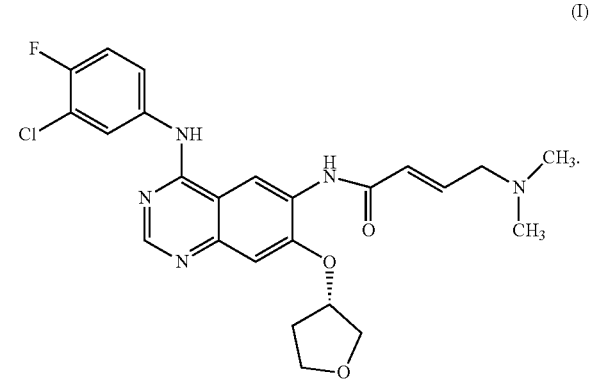

14 Claims, 8 Drawing Sheets

POLYMORPHS AND PROCESS FOR THE PREPARATION OF QUINAZOLINYL DERIVATIVES

FIELD OF THE INVENTION

The present invention relates to polymorphic forms of Afatinib or its pharmaceutically acceptable salts thereof, process for their preparation and pharmaceutical composition comprising it.

BACK GROUND OF THE INVENTION

Afatinib (coded as BIBW 2992), 2-Butenamide, N-[4-[(3-Chloro-4-fluorophenyl)amino]-7-[[(3S)-tetrahydro-3-furanyl]oxy]-6-quinazolinyl]-4(dimethylamino),(2E)- a compound of formula I is marketed as its dimaleate salt by Boehringer Ingelheim, under the trade name GILOTRIF®. Gilotrif® is an orally administered irreversible inhibitor of both the epidermal growth factor receptor (EGFR) and human epidermal receptor 2 (HER2) tyrosine kinases. Afatinib is under development for treatment of several solid tumors including non-small cell lung cancer (NSCLC), breast, head and neck cancer and a variety of other cancers.

Formula I

U.S. RE 43,431 (U.S. '431) discloses Afatinib and its physiologically acceptable salts. U.S. '431 discloses the preparation of Afatinib as follows.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

U.S. Pat. No. 8,426,586 B2 (U.S.'586) discloses the crystalline form of Afatinib dimaleate characterized by peaks at 2-theta 4.91, 6.42, 7.47, 8.13, 10.37, 17.19, 19.43, 19.91, 21.33, 22.94 and 25.56 and this crystalline form prepared using ethanol as solvent.

WO 2013/052157 A1 discloses the crystalline forms of Afatinib dimaleate designated as Form C, Form D, Form E, wherein Form C has been prepared from Tetrahydrofuran; Form D has been prepared from ethanol; Form E has been prepared by treating/exposing Form A to hygroscopicity under specific humidity conditions. Further, WO 2013/052157 A1 referred the crystalline form of U.S. '586 as Form A.

US 2014/0051713 A1 discloses the crystalline forms of Afatinib free base designated as Form A, Form B, Form C, Form D, wherein Form A has been prepared from ethyl acetate; Form B has been prepared from butylacetate and methylcyclohexane; Form C has been prepared from methylcyclohexane and n-butyl acetate; Form D has been prepared from n-butyl acetate and methylcyclohexane. In addition to the crystalline forms of Afatinib free base US 2014/0051713 A1 also discloses Afatinib dimaleate Form B and its preparation. WO 2015/007206 A1 discloses different salts of Afatinib, their polymorphs, Afatinib dimaleate crystalline Form N and was prepared using nitromethane.

IP.Com IPCOM000240150D published on Jan. 7, 2015 discloses Afatinib dimaleate crystalline form having characterization peaks at 2-theta 4.1, 5.0, 7.0, 8.1, 13.9, 17.5, 18.4, 20.5, 21.7 and 26.2 degrees+/−0.2 degrees 2-theta, wherein prepared using 2-Me-THF/2-propanol. Further this journal also discloses Afatinib free base crystalline Form I and Form II, wherein Form I has been prepared using ethanol and water; Form II has been prepared using ethanol.

In view of the above, it is understood that the solvent medium and mode of crystallization plays very important role in obtaining a polymorphic form, which is stable.

Afatinib and its dimaleate salt can exist in different polymorphic forms, which may differ from each other in terms of stability, physical properties, spectral data as well as process for the preparation thereof. However, there is still a need of new crystalline form, which is stable, reproducible, free of other polymorphic forms and suitable for pharmaceutical composition.

In view of this the present inventors have now found a process suitable industrially for preparing Afatinib and its pharmaceutically acceptable salt thereof as well as polymorphic forms of Afatinib free base, Afatinib dimaleate, which is stable, reproducible, free of other polymorphic forms and suitable for pharmaceutical composition. Further the present inventors have found that the major impurities formed during the manufacture process of Afatinib or pharmaceutically acceptable salts are Afatinib N-Oxide of formula II and hydrolytic cyclisation impurity of formula III as referred in Australian public assessment report (TGA) of Afatinib dimaleate and noticed that they are formed due to aerial oxidation/moisture sensitivity.

Formula II

Formula III

Further the present inventors have now found a process which controls the above referred impurities and provides Afatinib or its pharmaceutically acceptable salts thereof having high purity, stable with industrial acceptable yields.

OBJECTIVES OF THE INVENTION

The objective of the present invention is to provide crystalline form of Afatinib.

Another objective of the present invention is to provide crystalline form of Afatinib dimaleate.

Another objective of the present invention is to provide process for the preparation crystalline form of Afatinib and pharmaceutical composition comprising it.

Another objective of the present invention is to provide process for the preparation crystalline form of Afatinib dimaleate and pharmaceutical composition comprising it.

Another objective of the present invention is to provide amorphous form of Afatinib dimaleate, process for preparing amorphous form of Afatinib dimaleate and pharmaceutical composition comprising it.

Another objective of the present invention is to provide Afatinib or its pharmaceutically acceptable salts, which yields industrially acceptable yields, purity, economical, commercially feasible.

Another objective of the present invention is to provide Afatinib or its pharmaceutically acceptable salts with acceptable limits of impurities.

SUMMARY OF THE INVENTION

The present invention relates to Afatinib dimaleate crystalline form designated as Form H1 which is characterized by Powder X-Ray Diffraction, having the °2θ characteristic peaks at 5.0, 20.2, 25.6, 28.1±0.2 degrees.

In another embodiment the present invention relates to a process for the preparation of Afatinib dimaleate crystalline Form H1, which comprises:
  a. treating Afatinib base in polar aprotic solvent or mixtures thereof;
  b. adding maleic acid solution;
  c. maintaining for 4 hours; and
  d. isolating Afaitnib dimaleate crystalline Form H1.

The present invention relates to Afatinib dimaleate crystalline form designated as Form H2 which is characterized by Powder X-Ray Diffraction, having the °2θ characteristic peaks at 5.0, 5.4, 20.1, 25.8±0.2 degrees.

In another embodiment the present invention provides a process for the preparation of Afatinib dimaleate crystalline Form H2, which comprises:
- a. treating Afatinib base in polar aprotic solvent or mixtures thereof;
- b. adding maleic acid solution;
- c. maintaining for 9 hours; and
- d. isolating Afaitnib dimaleate crystalline Form H2.

The present invention relates to Afatinib dimaleate crystalline form designated as Form H3 which is characterized by Powder X-Ray Diffraction, having the °2θ characteristic peaks at 5.3, 18.1, 24.7±0.2 degree.

In another embodiment the present invention provides a process for the preparation of Afatinib dimaleate crystalline Form H3, which comprises:
- a. treating Afatinib base in a mixture of solvents selected from the group comprising of polar aprotic solvents, alcohols;
- b. cooling the reaction mass;
- c. adding maleic acid solution;
- d. optionally adding a solvent;
- e. maintaining for 1-2 hours; and
- f. isolating Afatinib dimaleate crystalline Form H3.

In another embodiment of the present invention relates to amorphous Afatinib dimaleate.

In another embodiment of the present invention provides a process for the preparation of amorphous Afatinib dimaleate, which comprises:
- a. treating Afatinib base in polar aprotic solvent or mixtures thereof;
- b. cooling the reaction mass;
- c. adding maleic acid solution;
- d. maintaining for 2 hours; and
- e. isolating amorphous Afatinib dimaleate.

The present invention relates to Afatinib free base crystalline form designated as Form H4 which is characterized by Powder X-Ray Diffraction, having the °2θ characteristic peaks at 5.3, 6.2, 12.3, 18.4±0.2 degrees.

In another embodiment the present invention provides a process for the preparation of Afatinib free base crystalline Form H4, which comprises:
- a. treating afatinib base in a non-polar solvent;
- b. optionally stirring; and
- c. isolating Afatinib free base crystalline Form H4.

The present invention relates to Afatinib free base crystalline form designated as Form H5, which is characterized by Powder X-Ray Diffraction, having the °2θ characteristic peaks at 6.1, 18.8, 23.6±0.2 degrees.

In another embodiment of the present invention provides a process for the preparation of Afatinib free base crystalline Form H5, which comprises:
- a. treating Afatinib base in a mixture of solvents selected from polar aprotic solvents, ethers;
- b. optionally maintaining for 1 hour; and
- c. isolating Afatinib free base crystalline Form H5.

In another embodiment of the present invention provides a pharmaceutical composition comprising crystalline form or amorphous form of Afatinib or its dimaleate salt.

In another embodiment of the present invention provides a process for the preparation of Afatinib dimaleate, which comprises:
- a. treating Afatinib base with a solvent;
- b. adding maleic acid solution; and
- b. isolating Afatinib dimaleate;
  wherein the solvent treated with an anti-oxidant.

In another embodiment of the present invention provides a process for the preparation of Afatinib free base crystalline form, which comprises:
- a. treating Afatinib base with an organic solvent or mixtures thereof;
- b. optionally adding water; and
- c. isolating Afatinib free base crystalline form;
  wherein organic solvent treated with an anti-oxidant.

Figure 1:
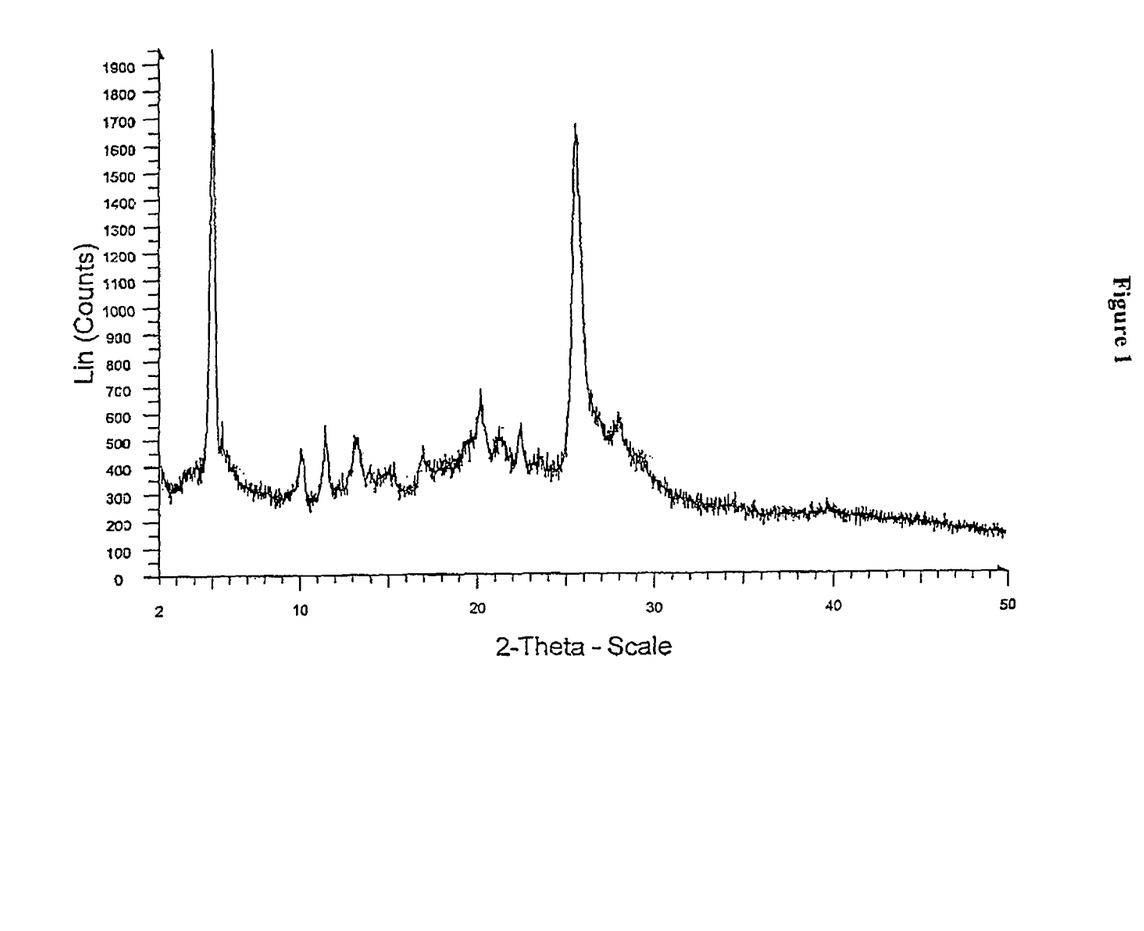
FIG. 1 shows powder X-ray diffractogram pattern of Afatinib dimaleate crystalline Form H1.
Figure 2:
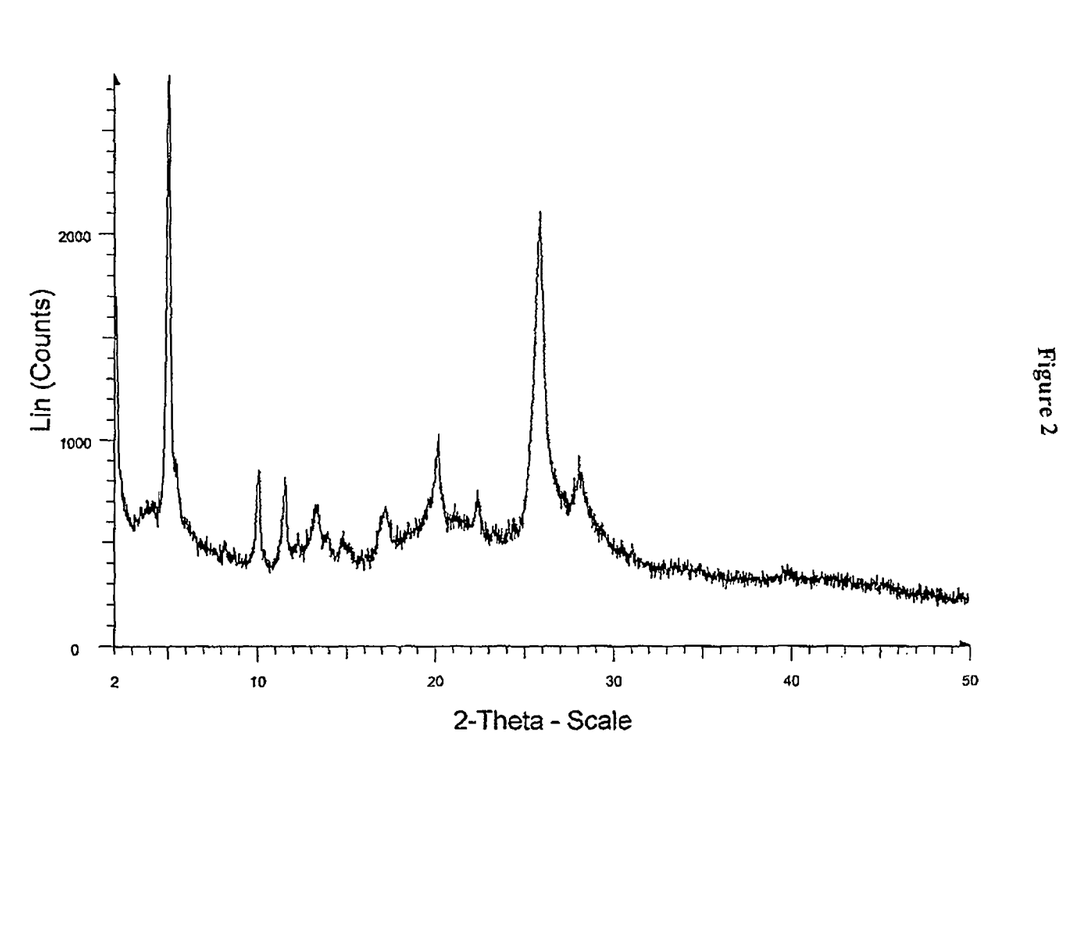
FIG. 2 shows powder X-ray diffractogram pattern of Afatinib dimaleate crystalline Form H2.
Figure 3:
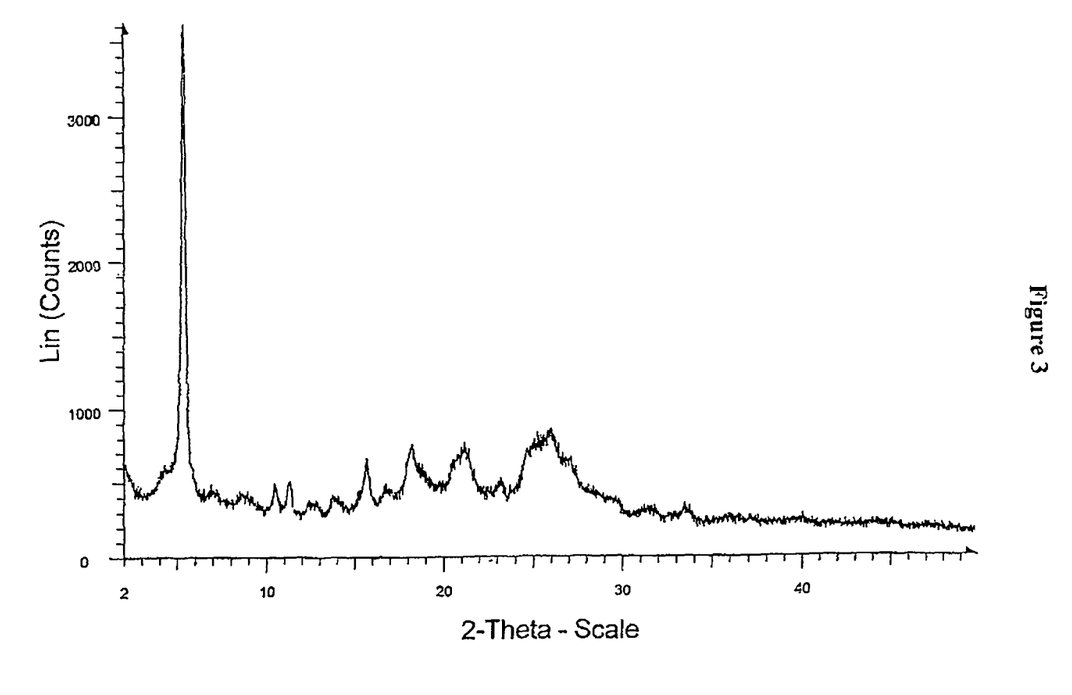
FIG. 3 shows powder X-ray diffractogram pattern of Afatinib dimaleate crystalline Form H3
Figure 4:
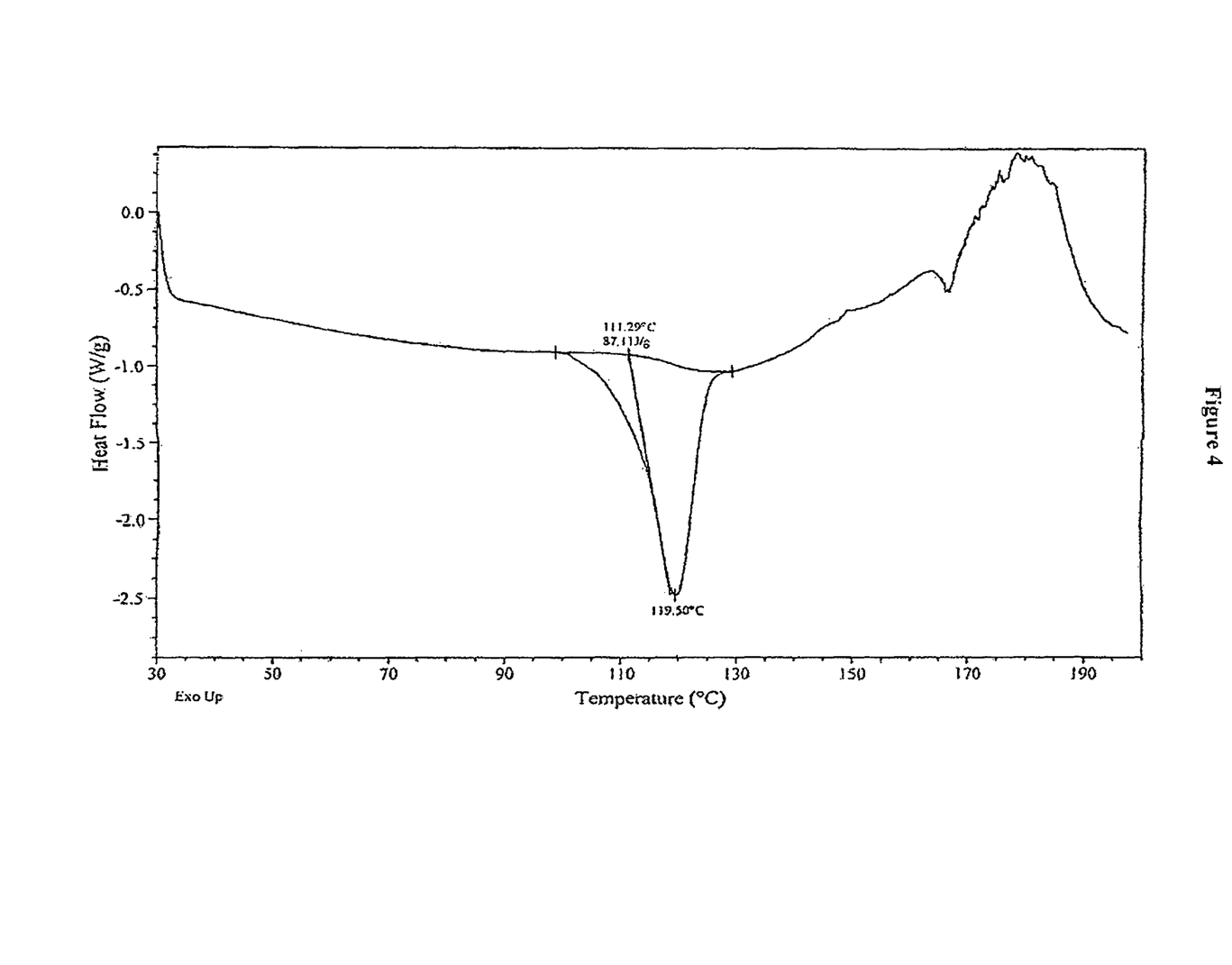
FIG. 4 shows a DSC of Afatinib dimaleate crystalline Form H3.
Figure 5:
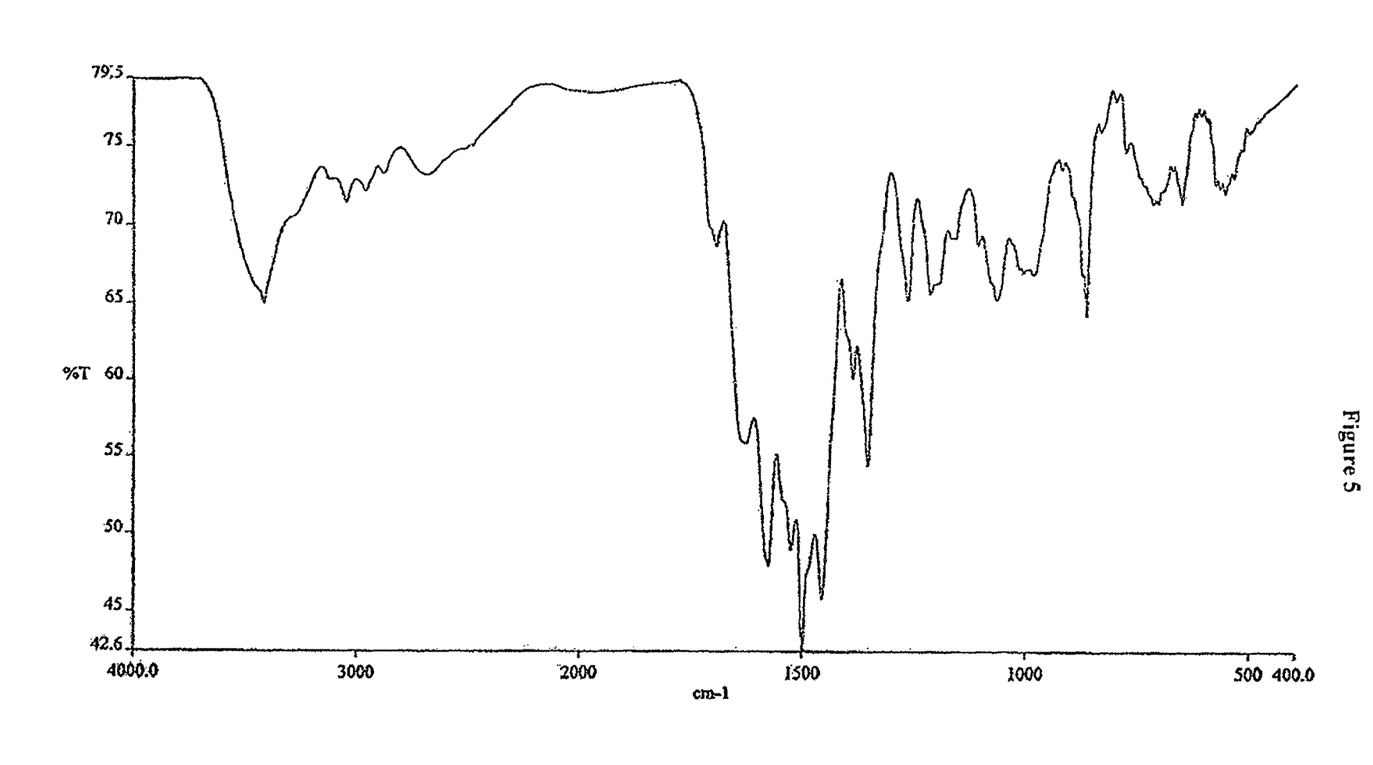
FIG. 5 shows IR of Afatinib dimaleate crystalline Form H3.
Figure 6:
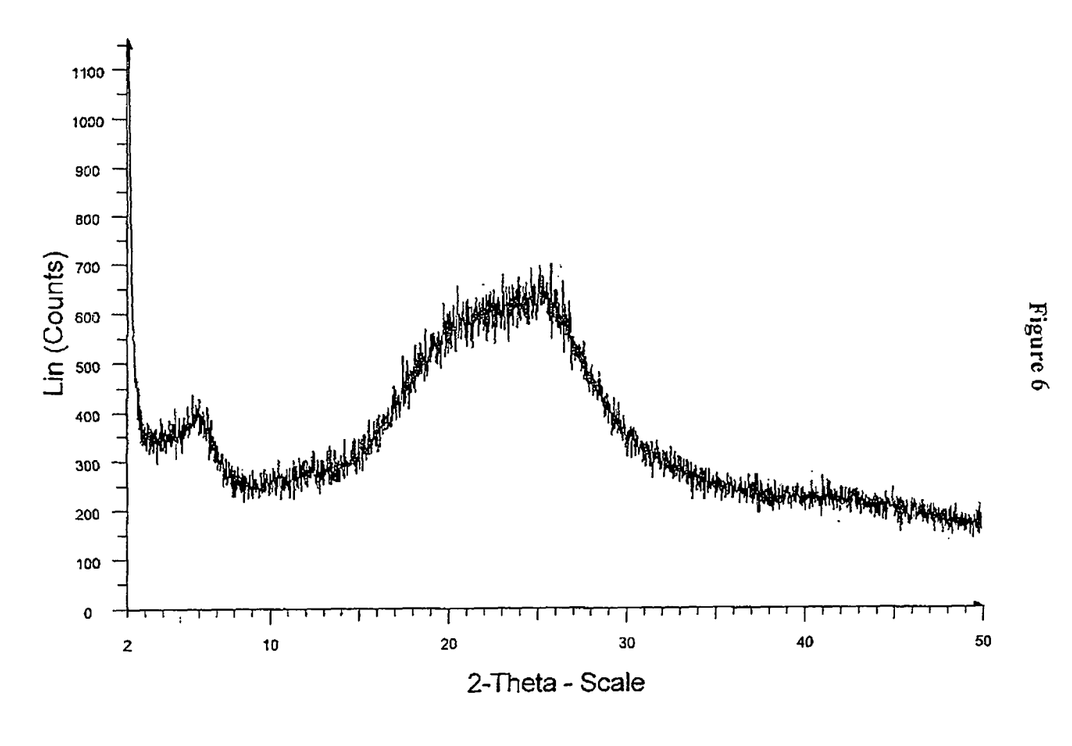
FIG. 6 shows powder X-ray diffractogram pattern of Afatinib dimaleate amorphous form.
Figure 7:
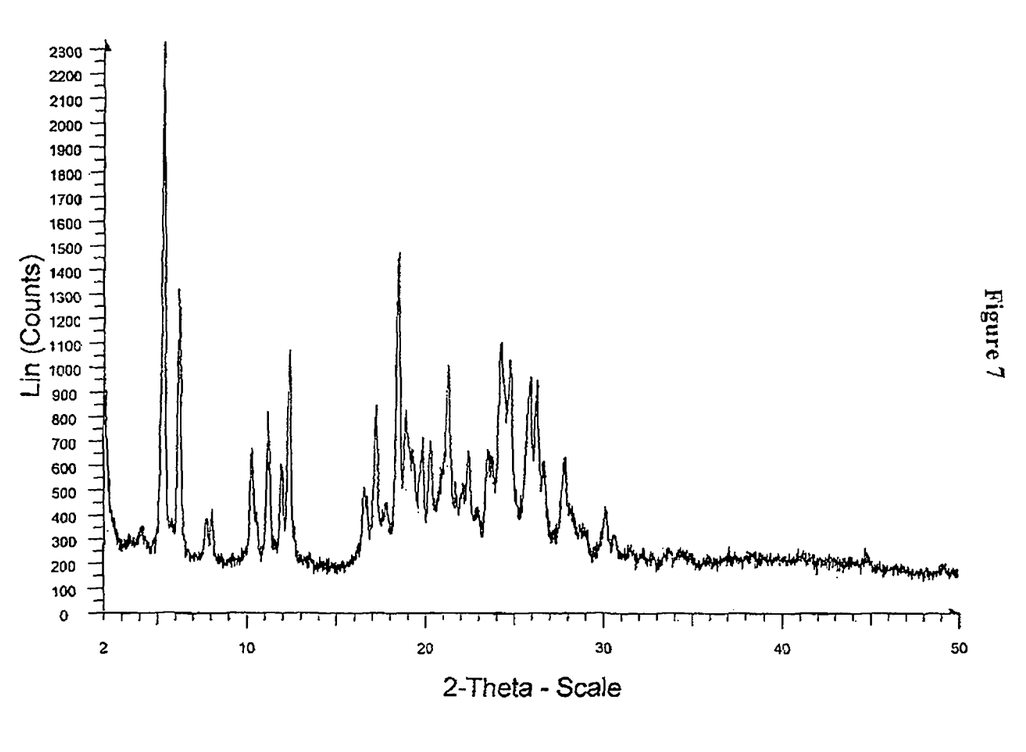
FIG. 7 shows powder X-ray diffractogram pattern of Afatinib free base crystalline Form H4.
Figure 8:
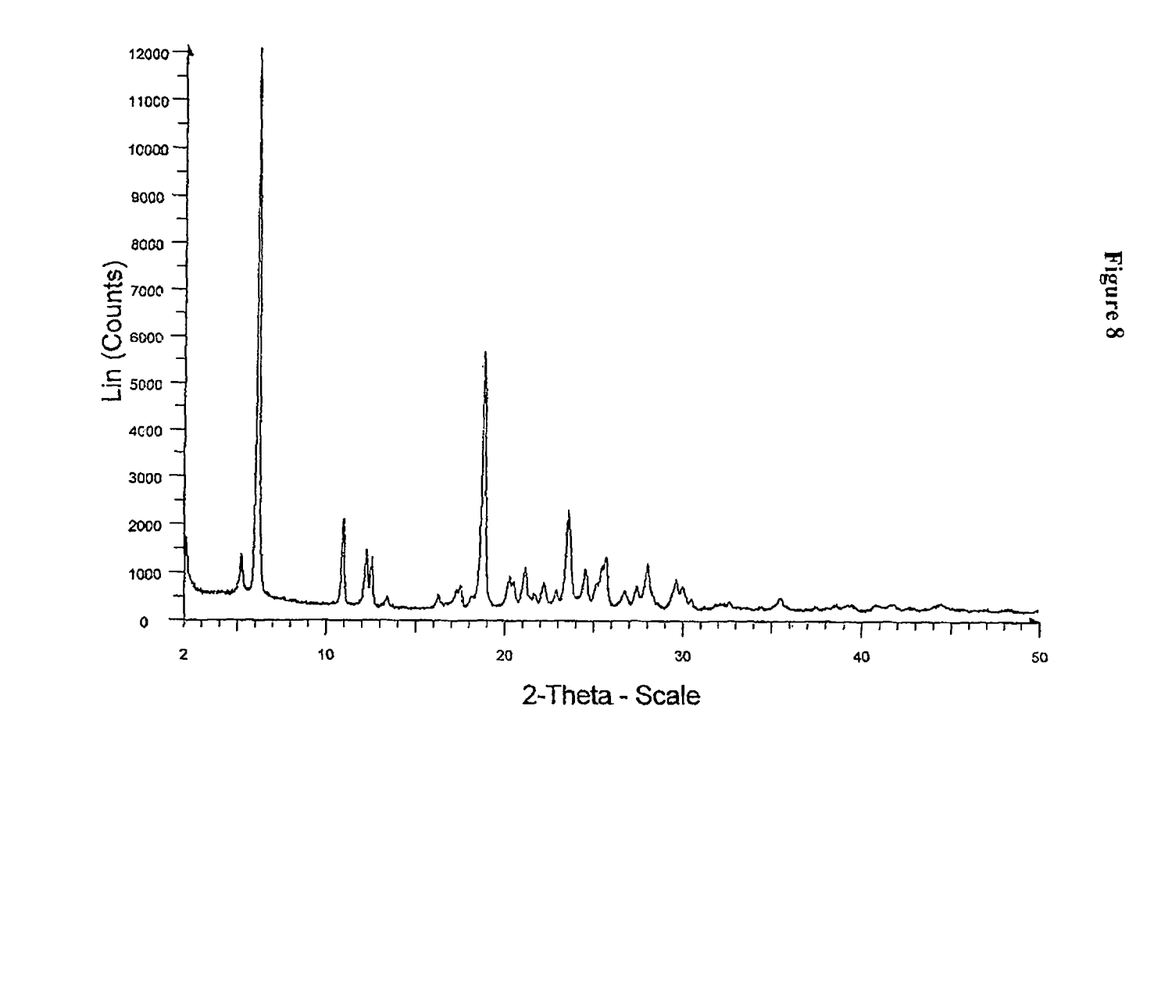
FIG. 8 shows powder X-ray diffractogram pattern of Afatinib free base crystalline Form H5.

X-ray powder diffraction spectrum was measured on a bruker axs D8 advance X-ray powder diffractometer having a copper-a radiation. Adequate sample was gently flattered on a sample holder and scanned from 2 to 50 degrees two-theta, at 0.02 increment and scan speed of 0.2 Sec/Step. The sample was simply placed on the sample holder. The sample was rotated at 30 rpm at a voltage 40 KV and current 35 mA.

DETAILED DESCRIPTION OF THE INVENTION

The present invention relates to new Afatinib dimaleate crystalline form designated as Form H1 having °2θ characteristic peaks at 5.0, 20.2, 25.6, 28.1±0.2 degrees, further characterized by having the peaks at 5.5, 11.4, 13.1, 22.4±0.2 degrees.

In another aspect of the present invention provides a process for the preparation of Afatinib dimaleate crystalline Form H1, which comprises treating Afatinib base in polar aprotic solvent or mixtures thereof, wherein polar aprotic solvent is selected from the group comprising of ketones, esters, nitriles, tetrahydrofuran, dimethyl sulfoxide, dimethyl formamide, halogenated hydrocarbons; adding maleic acid solution, prepared by dissolving maleic acid in a suitable solvent selected from polar aprotic solvents, wherein polar aprotic solvent is selected from the group comprising of ketones, esters, nitriles, tetrahydrofuran, dimethyl sulfoxide, dimethyl formamide, halogenated hydrocarbons; maintaining the reaction for 4 hours; and isolating Afaitnib dimaleate crystalline Form H1.

The present invention relates to new Afatinib dimaleate crystalline form designated as Form H2 having characteristic peaks at about having the 2θ characteristic peaks at 5.0, 5.4, 20.1, 25.8±0.2 degrees, further characterized by peaks at 10.0, 11.5, 19.6, 28.2±0.2 degrees.

In another aspect of the present invention, provides a process for the preparation of Afatinib dimaleate crystalline Form H2, which comprises treating Afatinib base in polar aprotic solvent or mixtures thereof, wherein polar aprotic solvent is selected from the group comprising of ketones, esters, nitriles, tetrahydrofuran, dimethyl sulfoxide, dimethyl formamide, halogenated hydrocarbons; adding maleic acid solution, prepared by dissolving maleic acid in a suitable solvent selected from polar aprotic solvents, wherein polar aprotic solvent is selected from the group comprising of ketones, esters, nitriles, tetrahydrofuran, dimethyl sulfoxide, dimethyl formamide, halogenated hydrocarbons; maintaining the reaction for 9 hours; and isolating Afaitnib dimaleate crystalline Form H2.

The present invention relates to new Afatinib dimaleate crystalline form designated as Form H3 having characteristic peaks at about having the characteristic °2θ, peaks at about 5.3, 13.7, 18.1, 23.2, 24.7, ±0.2 degrees.

In another aspect of the present invention provides a process for the preparation of Afatinib dimaleate crystalline Form H3, which comprises treating Afatinib base in a mixture of solvents selected from the group comprising of polar aprotic solvents, alcohols; wherein alcohols is selected from aliphatic alcohols selected from the group comprising of methanol, ethanol, n-propanol, isopropanol, n-butanol, pentanol, isobutanol, tertiary butanol, cyclopropanol, cyclobutanol, cyclopentanol, cyclohexanol or mixtures thereof, aromatic alcohols is selected from the group comprising of phenols, benzylalcohol or mixtures thereof; polar aprotic solvent is selected from the group comprising of ketones, esters, nitriles, tetrahydrofuran, dimethyl sulfoxide, dimethyl formamide, halogenated hydrocarbons; cooling the reaction mass to −25° to −50° C.; adding maleic acid solution; prepared by dissolving maleic acid in a suitable solvent selected from polar aprotic solvents, wherein polar aprotic solvent is selected from the group comprising of ketones, esters, nitriles, tetrahydrofuran, dimethyl sulfoxide, dimethyl formamide, halogenated hydrocarbons; optionally adding a solvent, wherein solvent is selected from polar aprotic solvent is selected from the group comprising of ketones, esters, nitriles, tetrahydrofuran, dimethyl sulfoxide, dimethyl formamide, halogenated hydrocarbons; maintaining the reaction for 1-2 hours; and thereafter isolating Afatinib dimaleate crystalline Form H3.

In another aspect of the present invention Afatinib dimaleate crystalline Form H3 is stable at 5±3° C. and 25±2° C./RH (Relative humidity) 60±5% and has the following stability data:

esters, nitriles, tetrahydrofuran, dimethyl sulfoxide, dimethyl formamide, halogenated hydrocarbons; maintaining for 2 hours; and isolating amorphous form of Afatinib dimaleate.

In another aspect of the present invention the isolation of amorphous Afatinib dimaleate is carried out by removing the solvent, wherein removal is carried out by distillation, spray drying, lyophilization, turbo drying.

The present invention also relates to Afatinib free base crystalline form designated as Form H4 having the characteristic peaks at 5.3, 6.2, 12.3, 18.4±0.2, further characterized by the peaks at 21.2, 24.2, 24.7, 25.8, 26.2±0.2 degrees.

In another aspect of the present invention provides a process for the preparation of Afatinib free base crystalline Form H4, which comprises treating afatinib base in a non-polar solvent; wherein non-polar solvent is selected from the group comprising of hydrocarbons, ethers;

optionally stirring; and isolating Afatinib free base crystalline Form H4.

The present invention relates to Afatinib free base crystalline form designated as Form H5 having characteristic peaks at 6.1, 18.8, 23.6±0.2, further characterized by peak at 10.9±0.2 degrees.

In another aspect the present invention provides a process for the preparation of Afatinib free base crystalline Form H5, which comprises treating Afatinib base in a mixture of solvents selected from polar aprotic solvents, ethers; wherein polar aprotic solvent is selected from the group comprising of ketones, esters, nitriles, tetrahydrofuran, dimethyl sulfoxide, dimethyl formamide, halogenated hydrocarbons, optionally maintaining for 1 hour; and isolating Afatinib free base crystalline Form H5.

In another aspect of the present invention Afatinib free base has been prepared by following the process known in the prior art.

In another aspect of the present invention Afatinib base may be solid, oil or gummy mass etc.

According to another aspect of the present invention, there is provided a pharmaceutical composition comprising crystalline Form H1 of Afatinib dimaleate and pharmaceutically acceptable excipients, and optionally other therapeutic ingredients. Afatinib dimaleate crystalline Form HI may

|  | PXRD | | Impurity | | Water Content | |
|---|---|---|---|---|---|---|
|  | 5 ± 3° C. | 25 ± 2° C./ RH 60 ± 5% | 5 ± 3° C. | 25 ± 2° C./ RH 60 ± 5% | 5 ± 3° C. | 25 ± 2° C./ RH 60 ± 5% |
| Initial | Form H3 | Form H3 | 0.22 | 0.22 | 1.0 | 1.0 |
| 1st Month | Form H3 | Form H3 | 0.22 | 0.22 | 1.34 | 1.18 |
| 2nd Month | Form H3 | Form H3 | 0.26 | 0.38 | 1.40 | 1.35 |
| 3rd Month | Form H3 | Form H3 | 0.27 | 0.43 | 1.26 | 1.56 |

According to another aspect of the present invention provides amorphous form of Afatinib dimaleate.

In another aspect of the present invention provides a process for the preparation of amorphous Afatinib dimaleate, which comprises treating Afatinib base in polar aprotic solvent or mixtures thereof; wherein polar aprotic solvent is selected from the group comprising of ketones, esters, nitriles, tetrahydrofuran, dimethyl sulfoxide, dimethyl formamide, halogenated hydrocarbons; cooling the reaction mass to 0 to −10° C.; adding maleic acid solution; prepared by dissolving maleic acid in a suitable solvent selected from polar aprotic solvents, wherein polar aprotic solvent is selected from the group comprising of ketones, preferably be formulated into tablets, capsules, suspensions, dispersions, injectables or other pharmaceutical forms.

According to another aspect of the present invention, there is provided a pharmaceutical composition comprising crystalline Form H2 of Afatinib dimaleate and pharmaceutically acceptable excipients, and optionally other therapeutic ingredients. Afatinib dimaleate crystalline Form H2 may preferably be formulated into tablets, capsules, suspensions, dispersions, injectables or other pharmaceutical forms.

According to another aspect of the present invention, there is provided a pharmaceutical composition comprising crystalline Form H3 of Afatinib dimaleate and pharmaceutically acceptable excipients, and optionally other therapeutic ingredients. Afatinib dimaleate crystalline Form H3 may preferably be formulated into tablets, capsules, suspensions, dispersions, injectables or other pharmaceutical forms.

According to another aspect of the present invention, there is provided a pharmaceutical composition comprising amorphous Afatinib dimaleate and pharmaceutically acceptable excipients, and optionally other therapeutic ingredients. Afatinib dimaleate amorphous Form may preferably be formulated into tablets, capsules, suspensions, dispersions, injectables or other pharmaceutical forms.

According to another aspect of the present invention, there is provided a pharmaceutical composition comprising crystalline Form H4 of Afatinib free base and pharmaceutically acceptable excipients, and optionally other therapeutic ingredients. Afatinib crystalline Form H4 may preferably be formulated into tablets, capsules, suspensions, dispersions, injectables or other pharmaceutical forms.

According to another aspect of the present invention, there is provided a pharmaceutical composition comprising crystalline Form H5 of Afatinib free base and pharmaceutically acceptable excipients, and optionally other therapeutic ingredients. Afatinib crystalline Form H5 may preferably be formulated into tablets, capsules, suspensions, dispersions, injectables or other pharmaceutical forms.

In another aspect the present invention provides a process for the preparation of Afatinib dimaleate, which comprises treating Afatinib base with a solvent, wherein solvent is selected from group comprising polar aprotic solvent, which is selected from the group comprising of ketones, esters, nitriles, tetrahydrofuran, dimethyl sulfoxide, dimethyl formamide, halogenated hydrocarbons; non-polar solvent is selected from the group comprising of hydrocarbons, ethers, alcohols; adding maleic acid solution, wherein maleic acid is dissolved in a solvent selected from polar aprotic solvent, wherein polar aprotic solvent is selected from the group comprising of ketones, esters, nitriles, tetrahydrofuran, dimethyl sulfoxide, dimethyl formamide, halogenated hydrocarbons; non-polar solvent is selected from the group comprising hydrocarbons, ethers; alcohols and isolating Afatinib dimaleate, wherein the solvent is treated with an anti-oxidant, wherein anti-oxidant is selected from butylated hydroxy toluene, butylated hydroxy anisole.

In another aspect the present invention provides a process for the preparation of Afatinib free base crystalline form, which comprises treating Afatinib base with an organic solvent, wherein organic solvent is selected from polar aprotic solvent, which is selected from the group comprising of ketones, esters, nitriles, tetrahydrofuran, dimethyl sulfoxide, dimethyl formamide, halogenated hydrocarbons; non-polar solvent is selected from the group comprising hydrocarbons, ethers, alcohols; optionally adding water; isolating Afatinib free base crystalline form, wherein organic solvent is treated with an anti-oxidant, wherein anti-oxidant is selected from butylated hydroxy toluene, butylated hydroxy anisole.

In another aspect of the present invention, anti-oxidant is used in an amount of 0.1 to 5% w/w wrt Afatinib.

According to another aspect of the present invention, process for the preparation of the Afatinib dimaleate having impurity of Formula II and Formula III designated above is present individually less than 1%, preferably less than 0.5%, more preferably "Not detected".

According to another aspect of the present invention, process for the preparation of the Afatinib dimaleate has the residual solvents within the ICH limits and following the present invention process yields the Afatinib dimaleate suitable commercially and industrially.

In another aspect of the present invention ketones used throughout the invention are aliphatic ketones selected from the group comprising acetone, diethyl ketone, methyl ethyl ketone, methyl isobutyl ketone and methyl propyl ketone, cyclobutanone, cyclopentanone, cyclohexanone or mixtures thereof; esters used throughout the invention are aliphatic esters or aromatic esters wherein aliphatic esters are selected from ethyl acetate, methyl acetate, isopropyl acetate, tert-butyl methyl acetate, ethyl formate or mixtures thereof; nitrile used throughout the invention are selected from the group comprising of aliphatic nitrile such as $C_2$-$C_8$ nitrile; alcohols used throughout the invention are selected from aliphatic alcohols selected from the group comprising of methanol, ethanol, n-propanol, isopropanol, n-butanol, pentanol, isobutanol, tertiary butanol, cyclopropanol, cyclobutanol, cyclopentanol, cyclohexanol or mixtures thereof, aromatic alcohols used throughout the invention are selected from the group comprising of phenols, benzylalcohol or mixtures thereof; ethers used throughout the invention are selected from the group comprising of symmetrical or asymmetrical ethers or cyclic ethers selected from diethyl ether, methyl tert-butyl ether, diisopropyl ether, tetrahydrofuran or mixtures thereof; halogenated hydrocarbons are selected from methylene dichloride, ethylene dichloride, chloroform, carbon tetrachloride or mixtures thereof; hydrocarbons selected from the group comprising aliphatic hydrocarbons comprising alkanes from $C_{1-7}$ alkanes, aromatic hydrocarbons selected from toluene, xylene or mixtures thereof and cycloalkanes selected from cyclohexane, cylcopentane or mixtures thereof, $C_{1-7}$ alkanes are selected from hexane, heptane or mixtures thereof.

In another aspect of the present invention mixture of solvents referred to two or more solvents.

In another aspect of the present invention isolation is carried out by known conventional methods.

In another aspect of the present invention Afatinib free base has been prepared by following the process known in the prior art.

In another embodiment of the present invention the Afatinib dimaleate crystalline form is packed in a clear polyethylene bag and tied with a thread, optionally placed in the primary packing inside a black color polyethylene bag and sealing it, further placed the above polyethylene bag inside a triple laminated bag, sealed under vacuuminised nitrogen atmosphere and placed in closed high density polyethylene (HDPE) container. The oxygen busters can be used inside the black color polyethylene bag and a triple laminated bag.

In the following section embodiments are described by way of examples to illustrate the process of invention. However, these do not limit the scope of the present invention. Variants of these examples would be evident to persons ordinarily skilled in the art.

EXAMPLES

Preparation of Afatinib

Reference Example 5.6 liters of 30% hydrochloric acid (53.17 mol) was added to 4.4 liters of water. Then 4.28 kg of 95% (dimethylamino)-acetaldehyde-diethyl-acetal (26.59 mol) was added dropwise within 20 minutes at 30 deg C. The solution is stirred for 8 hours at 35 deg C. stirred, cooled to 5 deg C. and stored under argon. This solution is referred to as solution B.

4.55 kg (68.06 mol) of Potassium hydroxide was dissolved in 23.5 liters of water and cooled to −5 deg C. This solution is referred to as solution C.

5.88 kg (10.63 mol) of diethyl ((4-(3-Chloro-4-fluoro-phenylamino)-7-(tetrahydrofuran-3-yloxy)-quinazoline-6-ylcarbamoyl)-methyl)-phosphonate and 0.45 kg of lithium chloride (10.63 mol) were placed in 23.5 liters of tetrahydrofuran and cooled to −7 deg C. The cold solution C was added within 10 minutes. Then solution B was added at −7 deg. C. within 1 hour. Stirred for a further hour at −5 deg C., heated to 30 deg C. and combined with 15 liters of water. After cooling to 3 deg C. the suspension was suction filtered, washed with water and dried. Yield: 5.21 kg of crude product, 100%, water content: 6.7%

The crystallisation of the crude product is carried out with butylacetate/methylcyclohexane Yield: 78% purity HPLC 99.4FI %, water content 5.4%.

Preparation of Afatinib Dimaleate Crystalline Form 6.0 kg (12.35 mol) of (E)-4-dimethylamino-but-2-enoic acid-(4-(3-chloro-4-fluoro-phenylamino)-7-((S)-tetrahydro-furan-3-yloxy)-quinazolin-6-yl)-amide are placed in 84 liters of ethanol and heated to 70° C. and combined with a solution of 2.94 kg (25.31 mol) of maleic acid in 36 liters of ethanol. After crystallisation has set in, first the mixture is cooled to 20° C. and stirred for 2 hours, then for 3 hours at 0° C. The precipitate is suction filtered, washed with 19 liters of ethanol and dried in vacuo at 40° C.

Yield: 8.11 kg (91.5%)
Melting point: 178° C.

Example 1

Preparation of Afatinib Dimaleate Crystalline Form H1

Afatinib free base (3.0 gm) was taken in methylisobutyl ketone (7.5 ml) at 20-25 deg C. and stirred for 15 minutes. Maleic acid (1.5 gm) was dissolved in Methylisobutylketone (7.5 ml) and added to the above reaction mass. Stirred for 4 hours. The solid obtained was filtered, washed with Methylisobutylketone and dried to yield Afatinib dimaleate crystalline Form H1.

Yield: 3.9 gm

Example 2

Preparation of Afatinib Dimaleate Crystalline Form H2

Afatinib free base (3.0 gm) was taken in methylisobutyl ketone (7.5 ml) at 20-25 deg C. and stirred for 15 minutes. Maleic acid (1.5 gm) was dissolved in Methylisobutylketone (30.0 ml) and added to the above reaction mass. Stirred for 9 hours. The solid obtained was filtered, washed with Methylisobutylketone and dried to yield Afatinib dimaleate crystalline Form H2.

Yield: 3.9 gm

Example 3

Preparation of Afatinib Dimaleate Crystalline Form H3

Afatinib free base (2.0 gm) was taken in Methylene dichloride (5.0 ml) and methanol (5.0 ml) and cooled to −25 deg C. Maleic acid (1.0 gm) was dissolved in ethylacetate (45.0 ml) and added to the above reaction mass at −25 deg C. Stirred for 2 hours at −25 deg C. The solid obtained was filtered, washed with ethylacetate and dried to yield Afatinib dimaleate Form H3.

Yield: 2.6 gm
Chromatographic Purity (by HPLC): 99.8%

Example 4

Preparation of Afatinib Dimaleate Crystalline Form H3

Afatinib free base (300 gm) was taken in Methylene dichloride (600 ml) and methanol (600 ml) and cooled to −35 deg C. Maleic acid (150 gm) was dissolved in ethylacetate (6600 ml) and added to the above reaction mass at −35 deg C. Stirred for 1 hour at −35 deg C. to −45 deg C. The solid obtained was filtered, washed with ethylacetate and dried to yield Afatinib dimaleate crystalline form.

Yield: 380 gm.
Chromatographic Purity (by HPLC): 99.8%

Example 5

Preparation of Amorphous Afatinib Dimaleate

Afatinib free base (2.0 gm) was taken in methylisobutyl ketone (5.0 ml) at 20-25 deg C. and cooled to −10 deg C. Maleic acid (1.0 gm) was dissolved in Methylisobutylketone (40.0 ml) and added to the above reaction mass at −10 deg C. Stirred for 2 hours at −10 deg C. The solid obtained was filtered, washed with Methylisobutylketone and dried to yield amorphous Afatinib dimaleate.

Yield: 2.6 gm

Example 6

Preparation of Afatinib Free Base Form H4

Afatinib free base (20.0 gm) was taken in cyclohexane (150 ml) and stirred for 30 minutes. The solid obtained was filtered, washed with cylcohexane and dried to yield Afatinib free base crystalline Form H4.

Yield: 17.5 gm

Example 7

Preparation of Afatinib Free Base Form H5

Afatinib free base (17.5 gm) was taken in acetone (70.0 ml) and diisopropyl ether (175 ml) at 20-25 deg C. and stirred for 1 hour. The solid obtained was filtered, washed with diisopropyl ether and dried to yield Afatinib free base crystalline Form H5.

Yield: 12.0 gm

Example 8

Preparation of Afatinib Free Base

Afatinib free base was slurried in diisopropylether (150 ml) added with butylated hydroxytoluene and dried to yield 75 gm of Afatinib free base crystalline form. Afatinib N-oxide by HPLC: 0.11%.

Example 9

Preparation of Afatinib Free Base

Afatinib free base (100 gm) was taken in tetrahydrofuran (500 ml) added with butylated hydroxytoluene (2.5 gm) at room temperature. Heated to 35-40 deg C. and stirred for 30 minutes. Added Butylated hydroxytoluene (2.75 gm) dissolved in Diisopropylether (550 ml) slowly for 60 minutes, stirred and cooled to room temperature. The solid thus obtained was filtered, washed with Diisopropylether (100 ml) added with Butylated hydroxytoluene (2.75 gm) and dried to yield 70 gm of Afatinib free base crystalline form. Afatinib N-oxide by HPLC: 0.07%.

Example 10

Preparation of Afatinib Free Base

Afatinib free base (100 gm) was taken in dimethylformamide (1000 ml) added with butylated hydroxytoluene (5 gm) at room temperature and stirred for 15 minutes. Added water (750 ml) slowly for 60 minutes and stirred for 45 minutes to 1 hour. The solid thus obtained was washed with dimethylformamide (50 ml) added with butylated hydroxytoluene (0.2 gm), water (37.5 ml) and dried to yield 85 gm of crystalline Afatinib free base. Afatinib N-oxide by HPLC: 0.08%.

We claim:

1. An Afatinib solid Form selected from the group consisting of:
    Afatinib dimaleate crystalline Form H1 characterized by Powder X-Ray Diffraction, having the ° 2θ characteristic peaks at 5.0, 20.2, 25.6, 28.1±0.2 degrees;
    Afatinib dimaleate crystalline Form H2 characterized by Powder X-Ray Diffraction, having the ° 2θ characteristic peaks at 5.0, 5.4, 20.1, 25.8±0.2 degrees;
    Afatinib dimaleate crystalline Form H3 characterized by Powder X-Ray Diffraction, having the ° 2θ characteristic peaks at 5.3, 18.1, 24.7±0.2 degrees;
    Afatinib free base crystalline form Form H4 which is characterized by Powder X-Ray Diffraction, having the ° 2θ characteristic peaks at 5.3, 6.2, 12.3, 18.4±0.2 degrees; and
    Afatinib free base crystalline form Form H5, which is characterized by Powder X-Ray Diffraction, having the ° 2θ characteristic peaks at 6.1, 18.8, 23.6±0.2 degrees.

2. A process for the preparation of the Afatinib dimaleate crystalline Form H1 of claim 1, which comprises:
    a. treating Afatinib base in polar aprotic solvent or mixtures thereof;
    b. adding maleic acid solution;
    c. maintaining for 4 hours; and
    d. isolating Afatinib dimaleate crystalline Form H1,
wherein the polar aprotic solvent is selected from the group comprising of ketones, esters, nitriles, tetrahydrofuran, dimethyl sulfoxide, dimethyl formamide, halogenated hydrocarbons, wherein the ketone is selected from the group consisting of acetone, diethyl ketone, methyl ethyl ketone, methyl isobutyl ketone and methyl propyl ketone, cyclobutanone, cyclopentanone, cyclohexanone; esters are selected from group consisting of aliphatic esters, aromatic esters; wherein aliphatic esters are selected from group consisting of ethyl acetate, methyl acetate, isopropyl acetate, tert-butyl methyl acetate, ethyl formate; nitrile is selected from the group consisting of aliphatic $C_2$-$C_8$ nitrile; halogenated hydrocarbons selected from methylene dichloride, ethylene dichloride, chloroform, carbon tetrachloride and/or mixtures thereof,
    wherein the Afatinib dimaleate crystalline Form H1 characterized by Powder X-Ray Diffraction, having the ° 2θ characteristic peaks at 5.0, 20.2, 25.6, 28.1±0.2 degrees.

3. A process for the preparation of the Afatinib dimaleate crystalline Form H2 of claim 1, which comprises:
    a. treating Afatinib base in polar aprotic solvent or mixtures thereof;
    b. adding maleic acid solution;
    c. maintaining for 9 hours; and
    d. isolating Afatinib dimaleate crystalline Form H2,
wherein the polar aprotic solvent is selected from the group comprising of ketones, esters, nitriles, tetrahydrofuran, dimethyl sulfoxide, dimethyl formamide, halogenated hydrocarbons,
    further wherein the ketone is selected from the group consisting of acetone, diethyl ketone, methyl ethyl ketone, methyl isobutyl ketone and methyl propyl ketone, cyclobutanone, cyclopentanone, cyclohexanone; esters are selected from group consisting of aliphatic esters, aromatic esters; wherein aliphatic esters are selected from group comprising of ethyl acetate, methyl acetate, isopropyl acetate, tert-butyl methyl acetate, ethyl formate; nitrile is selected from the group consisting of aliphatic $C_2$-$C_8$ nitrile; halogenated hydrocarbons selected from methylene dichloride, ethylene dichloride, chloroform, carbon tetrachloride and/or mixtures thereof,
    wherein the Afatinib dimaleate crystalline Form H2 characterized by Powder X-Ray Diffraction, having the ° 2θ characteristic peaks at 5.0, 5.4, 20.1, 25.8±0.2 degrees.

4. A process for the preparation of the Afatinib dimaleate crystalline Form H3 of claim 1, which comprises:
    a. treating Afatinib base in a mixture of solvents, selected from the group comprising of polar aprotic solvents, alcohols;
    b. cooling the reaction mass;
    c. adding maleic acid solution;
    d. optionally adding a solvent;
    e. maintaining for 1-2 hours; and
    f. isolating Afatinib dimaleate crystalline Form H3,
wherein the polar aprotic solvent is selected from the group comprising of ketones, esters, nitriles, tetrahydrofuran, dimethyl sulfoxide, dimethyl formamide, halogenated hydrocarbons,
    further wherein the ketone is selected from the group consisting of acetone, diethyl ketone, methyl ethyl ketone, methyl isobutyl ketone and methyl propyl ketone, cyclobutanone, cyclopentanone, cyclohexanone; esters are selected from group consisting of aliphatic esters, aromatic esters; wherein aliphatic esters are selected from group comprising of ethyl acetate, methyl acetate, isopropyl acetate, tert-butyl methyl acetate, ethyl formate; nitrile is selected from the group consisting of aliphatic $C_2$-$C_8$ nitrile; halogenated hydrocarbons selected from methylene dichloride, ethylene dichloride, chloroform, carbon tetrachloride and/or mixtures thereof,
    wherein the Afatinib dimaleate crystalline Form H3 characterized by Powder X-Ray Diffraction, having the ° 2θ characteristic peaks at 5.3, 18.1, 24.7±0.2 degrees.

5. A process for the preparation of the Afatinib free base crystalline Form H4 of claim 1, which comprises:
    a. treating Afatinib base in a non-polar solvent;
    b. optionally stirring; and
    c. isolating Afatinib free base crystalline Form H4, wherein the Afatinib free base crystalline form Form H4 which is characterized by Powder X-Ray Diffraction, having the ° 2θ characteristic peaks at 5.3, 6.2, 12.3, 18.4±0.2 degrees.

6. A process for the preparation of the Afatinib free base crystalline Form H5 of claim 1, which comprises:
    a. treating Afatinib base in a mixture of solvents selected from polar aprotic solvents, ethers;
    b. optionally maintaining for 1 hour; and
    c. isolating Afatinib free base crystalline Form H5, wherein polar aprotic solvent is selected from the group comprising of ketones, esters, nitriles, tetrahydrofuran, dimethyl sulfoxide, dimethyl formamide, halogenated hydrocarbons,
- further wherein the ketone is selected from the group consisting of acetone, diethyl ketone, methyl ethyl ketone, methyl isobutyl ketone and methyl propyl ketone, cyclobutanone, cyclopentanone, cyclohexanone; esters are selected from group consisting of aliphatic esters, aromatic esters; wherein aliphatic esters are selected from group consisting of ethyl acetate, methyl acetate, isopropyl acetate, tert-butyl methyl acetate, ethyl formate; nitrile is selected from the group comprising of aliphatic $C_2$-$C_8$ nitrile; halogenated hydrocarbons selected from methylene dichloride, ethylene dichloride, chloroform, carbon tetrachloride and/or mixtures thereof,
- wherein the Afatinib free base crystalline form Form H5, which is characterized by Powder X-Ray Diffraction, having the ° 2θ characteristic peaks at 6.1, 18.8, 23.6±0.2 degrees.

7. The process according to claim 4, wherein the alcohol is selected from aliphatic alcohols selected from the group consisting of methanol, ethanol, n-propanol, isopropanol, n-butanol, pentanol, isobutanol, tertiary butanol, cyclopropanol, cyclobutanol, cyclopentanol, cyclohexanol, aromatic alcohols are selected from the group comprising of phenols, benzylalcohol and/or mixture thereof.

8. The process according to claim 5, wherein non-polar solvent is selected from the group consisting of hydrocarbons, ethers and/or mixture thereof.

9. The process according to claim 8, wherein ethers is selected from the group comprising of symmetrical or asymmetrical ethers, cyclic ethers selected from the group consisting of diethyl ether, methyl tert-butyl ether, diisopropyl ether, tetrahydrofuran; hydrocarbons is selected from the group consisting of aliphatic hydrocarbons comprising alkanes from $C_{1-7}$ alkanes; aromatic hydrocarbons is selected from toluene, xylene; cycloalkanes selected from cyclohexane, cyclopentane, $C_{1-7}$ alkanes selected from hexane, heptane and/or mixtures thereof.

10. A pharmaceutical composition comprising the solid form of Afatinib of claim 1.

11. A process for the preparation of Afatinib dimaleate, which comprises:
   a. treating Afatinib base with a solvent;
   b. adding maleic acid solution; and
   b. isolating Afatinib dimaleate;
wherein the solvent treated with an anti-oxidant, wherein the anti-oxidant is selected from the group consisting of butylated hydroxy toluene, butylated hydroxy anisole, further wherein the anti-oxidant is used in an amount of 0.1 to 5% w/w wrt Afatinib.

12. The process according to claim 11, wherein the solvent is selected from group comprising of polar aprotic solvent, which is selected from the group consisting of ketones, esters, nitriles, tetrahydrofuran, dimethyl sulfoxide, dimethyl formamide, halogenated hydrocarbons; non-polar solvent is selected from the group consisting of hydrocarbons, ethers; alcohols.

13. A process for the preparation of Afatinib free base crystalline form, which comprises:
   a. treating Afatinib base with an organic solvent or mixtures thereof;
   b. optionally adding water; and
   c. isolating Afatinib free base crystalline form;
wherein organic solvent treated with an anti-oxidant, wherein the anti-oxidant is selected from the group consisting of butylated hydroxy toluene, butylated hydroxy anisole, further wherein the anti-oxidant is used in an amount of 0.1 to 5% w/w wrt Afatinib.

14. The process according to claim 13, wherein the solvent is selected from group comprising of polar aprotic solvent, which is selected from the group consisting of ketones, esters, nitriles, tetrahydrofuran, dimethyl sulfoxide, dimethyl formamide, halogenated hydrocarbons; non-polar solvent is selected from the group consisting of hydrocarbons, ethers; alcohols.

* * * * *